US007504096B1

(12) United States Patent
Stewart et al.

(10) Patent No.: US 7,504,096 B1
(45) Date of Patent: Mar. 17, 2009

(54) METHODS FOR IN VITRO FERTILIZATION (75) Inventors: Colin L. Stewart, Montclair, NJ (US); Teresa Shatzer, Inwood, WV (US); Teresa Sullivan, Myersville, MD (US); Jim-Ray Chen, Tao Yuan (TW); Lidia Hernandez, Montgomery Village, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/720,416

(22) PCT Filed: Jun. 30, 1999

(86) PCT No.: PCT/US99/14841

§ 371 (c)(1),
(2), (4) Date: Aug. 2, 2001

(87) PCT Pub. No.: WO00/01404

PCT Pub. Date: Jan. 13, 2000

(51) Int. Cl.
*A61K 38/19* (2006.01)
(52) U.S. Cl. .................................. 424/85.1; 514/2
(58) Field of Classification Search .................. None
See application file for complete search history.

(56) References Cited

U.S. PATENT DOCUMENTS

| 5,187,077 | A |   | 2/1993  | Gearing et al. |         |
|-----------|---|---|---------|----------------|---------|
| 5,340,740 | A |   | 8/1994  | Petitte et al. |         |
| 5,366,888 | A | * | 11/1994 | Fry et al.     | 435/375 |
| 5,418,159 | A | * | 5/1995  | Gough et al.   | 435/377 |
| 5,427,925 | A |   | 6/1995  | Gearing et al. |         |
| 5,443,825 | A |   | 8/1995  | Gearing et al. |         |
| 5,453,357 | A |   | 9/1995  | Hogan          |         |
| 5,641,676 | A |   | 6/1997  | Gough et al.   |         |
| 5,656,479 | A |   | 8/1997  | Petitte et al. |         |
| 5,670,372 | A |   | 9/1997  | Hogan          |         |
| 5,712,156 | A |   | 1/1998  | Fry et al.     |         |

FOREIGN PATENT DOCUMENTS

| WO | WO 95/13393    | 5/1995  |
| WO | WO 95/20661    | 8/1995  |
| WO | WO 96/01319    | 1/1996  |
| WO | WO 96/18648    | 6/1996  |
| WO | WO 96/33740    | 10/1996 |
| WO | WO-97/16202 A1 | 5/1997  |
| WO | WO 97/20035    | 6/1997  |
| WO | WO 97/42312    | 11/1997 |
| WO | WO-98/27996 A1 | 7/1998  |
| WO | WO 9827996     | * 7/1998 |

OTHER PUBLICATIONS

Elsner et al. (1997) "Multiple pregnancy rate and embryo number transferred during in vitro fertilization," Am. J. Obstet. Gynecol. 177:350-355.

MacDougall et al. (1992) "In-vitro fertilization and the ovarian hyperstimulation syndrome," Hum. Reprod. 7:597-600.

Taga and Kishimoto (1992) "Cytokine receptors and signal tansduction," FASEB J. 6:3387-3396.

Stewart et al. (1992) "Blastocyst implantation depends on maternal expression of leukaemia inhibitory factor," Nature 359:76-79.

Yamasaki et al. (1988) "Cloning and expression of the human interleukin-6 (BSF-2/IFN β2) receptor," Science 241:825-828.

Dunglison et al. (1996) "Leukaemia inhibitory factor significantly enhances the blastocyst formation rates of human embryos cultures in serum-free medium," Human Repro. 11:191-196.

Jurisicova et al. (1995) "Recombinant human leukemia inhibitory factor does not enhance in vitro human blastocyst formation," Fertility and Sterility 64:999-1002.

Borini et al. (1997) "Use of Recombinant Leukemia Inhibitory Factor in Embryo Implantation," Ann. N.Y. Acad. of Sci. 828:157-161.

Ace and Okulicz (1995) "Differential gene regulation by estrogen and progesterone in the primate endometrium," Mol. and Cell. Endo. 115:95-103.

Bhatt et al. (1991) "Uterine expression of leukemia inhibitory factor coincides with the onset of blastocyst implantation," Proc. Natl. Acad. Sci. 88:11408-11412.

Fischer et al. (1997) "A bioactive designer cytokine for human hematopoietic progenitor cell expansion," Nature Biotech. 15:142-145.

Hambartsoumian (1998) "Endometrial Leukemia Inhibitory Factor (LIF) as a Possible Cause of Unexplained Infertility and Multiple Failures of Implantation," Amer. J. Repro. Immunol. 39:137-143.

Hibi et al. (1990) "Molecular Cloning and Expression of an IL-6 Signal Transducer, gp130," Cell 63:1149-1157.

Lavranos et al. (1995) "Trophic effects of myeloid leukaemia inhibitory factor (LIF) on mouse embryos," J. Repro. and Fertility 105:331-338.

Stewart (1994) "Leukaemia Inhibitory Factor and the Regulation of Pre-Implantation Development of the Mammalian Embryo," Mol. Repro. and Dev. 39:233-238.

(Continued)

*Primary Examiner*—Prema Mertz
(74) *Attorney, Agent, or Firm*—Schwegman, Lundberg & Woessner, P.A.

(57) ABSTRACT

Compositions and methods are described to enhance embryo implantation. Cytokines capable of binding to a receptor complex (the complex comprising a member of the hematopoietic cytokine receptor family) are utilized to treat female mammals, and in particular, females receiving in vitro fertilized embryos.

3 Claims, 3 Drawing Sheets

OTHER PUBLICATIONS

Stewart and Cullinan "Preimplantation Development of the Mammalian Embryo and Its Regulation by Growth Factors," Dev. Genetics 21:91-101.

Yang et al. (1996) "Differential Hormonal Regulation of Leukemia Inhibitory Factor (LIF) in Rabbit and Mouse Uterus," Mol. Repro. and Dev. 43:470-476.

"LIF," Leukaemia Inhibitory Factor (LIF), pp. 124-126.

"LIF Receptor," Receptors for Leukaemia Inhibitory Factor (LIF) and Oncostaint M (OSM), pp. 130-133.

"Canadian Patent Application No. 2,333,307, Office Action mailed Oct. 8, 2002", 3 pgs.

"Canadian Patent Application No. 2,333,307, Office Action mailed Mar. 26, 2004", 5 pgs.

"Canadian Patent Application No. 2,333,307, Response filed Apr. 8, 2003 to Office Action mailed Oct. 8, 2002", 39 pgs.

"Canadian Patent Application No. 2,333,307, Response filed Sep. 23, 2004 to Office Action mailed Mar. 26, 2004", 23 pgs.

"European Patent Application No. 99932112.8, Communication mailed Jul. 30, 2007", 6 pgs.

"European Patent Application No. 99932112.8, Communication mailed Apr. 10, 2006", 8 pgs.

"European Patent Application No. 99932112.8, Communication mailed May 9, 2005", 5 pgs.

"European Patent Application No. 99932112.8, Response filed Nov. 23, 2004", 1 pg.

"European Patent Application No. 99932112.8, Response filed Aug. 3, 2006 to Communication mailed Apr. 10, 2006", 7 pgs.

"European Patent Application No. 99932112.8, Response filed Sep. 16, 2005 to Communication mailed May 9, 2005", 11 pgs.

"European Patent Application No. 99932112.8, Supplemental European Search Report mailed Sep. 29, 2004", 5 pgs.

"PCT Application No. PCT/US99/14841, International Preliminary Examination Report mailed May 25, 2000", 5 pgs.

"PCT Application No. PCT/US99/14841, International Search Report mailed Oct. 7, 1999", 2 pgs.

Chen, J. R., et al., "Leukemia Inhibitory Factor Can Substitute for Nidatory Estrogen and Is Essential to Inducing a Receptive Uterus for Implantation But Is Not Essential for Subsequent Embryogenesis", *Endocrinology*, 141(12), (Dec. 2000),4365-4372.

Hirano, T., et al., "Signal Transduction through gp130 that is shared among the Receptors for the Interleukin 6 related Cytokine Subfamily", *Stem Cells*, 12, (1994),262-277.

"PCT Application No. PCT/US99/14841, International Search Report mailed Oct. 7, 1999", 2 pgs.

"European Patent Application No. 99932112.8, Response filed Nov. 27, 2007 to Communication mailed Jul. 30, 2007", 18 pgs.

Akiyama, Y., et al., "In vivo Effect of Recombinant Human Leukemia Inhibitory Factor in Primates", *Jpn. J. Cancer Res.*, 88, (1997),578-583.

* cited by examiner

```
           10         20         30         40         50       # 60
M  MKVLAAGIVPLLLLVLHWKHGAGSPLPITPVNATCAIRHPCHGNLMNQIKNQLAQLNGSA
R  MKVLAAGIVP-LLLILVLHWKHGAGSPLPITPVNATCAIRHPCHGNLMNQIKSQLAQLNGSA
H  MKVLAAGVVP-LLLVLVLHWKHGAGSPLPITPVNATCAIRHPCHNNLMNQIRSQLAQLNGSA
O  MKILAAGVVP-LLLVLVLHWKPGAGSPLPINPVNATCNTHHPCPSNLMSQIRSQLAQLNGTA
P  MKVLAAGVVP-LLLVLVLHWKHGAGSPLSITPVNATCATRHPCHSNLMNQIKNQLAHVNSSA

70       # 80       # 90     # 100        110        #
M  NALFISYYTAQGEPFPNNVEKLCAPNMTDFPSFHGNGTEKTKLVELYRMVAYLSASLTNI
R  NALFISYYTAQGEPFPNNVDKLCAPNMTDFPPFHANGTEKTKLVELYRMVTYLGASLTNI
H  NALFILYYTAQGEPFPNNLDKLCGPNVTDFPPFHANGTEKAKLVELYRIVVYLGTSLGNI
O  NALFILYYTAQGEPFPNNLDKLCGPNVTDFPPFQPNGTEKVRLVELYRIVAYLGTALGNI
P  NALFILYYTAQGEPFPNNLDKLCGPNVTNFPPFHANGTEKARLVELYRIIAYLGASLGNI

#        150        160        170        180
M  TRDQKVLNPTAVSLQVKLNATIDVMRGLLSNVLCRLCNKYRVGHVDVPPVPDHSDKEAFQ
R  TWDQKNLNPTAVSLQIKLNATTDVMRGLLSSVLCRLCNKYHVGHVDVPCVPDNSSKEAFQ
H  TRDQKILNPSALSLHSKLNATADILRGLLSNVLCRLCSKYHVGHVDVTYGPDTSGKDVFQ
O  TRDQKTLNPTAHSLHSKLNATADTLRGLLSNVLCRLCSKYHVAHVDVAYGPDTSGKDVFQ
P  TRDQRSLNPGAVNLHSKLNATADSMRGLLSNVLCRLCNKYHVAHVDVAYGPLTSGKDVFQ 190        200
M  RKKLGCQLLGTYKQVISVVVQAF
R  RKKLGCQLLGTYKQVISVVVQAF
H  KKKLGCQLLGKYKQIIAVLAQAF
O  KKKLGCQLLGKYKQVMAVLAQAF
P  KKKLGCQLLGKYKQVISVLARAF
```

Figure 3

SEQUENCE LISTING

<160> NUMBER OF SEQ ID NOS: 9

<210> SEQ ID NO 1
<211> LENGTH: 202
<212> TYPE: PRT
<213> ORGANISM: Homo sapiens

<400> SEQUENCE: 1

```
Met Lys Val Leu Ala Ala Gly Val Val Pro Leu Leu Val Leu His
  1               5                  10                  15

Trp Lys His Gly Ala Gly Ser Pro Leu Pro Ile Thr Pro Val Asn Ala
                 20                  25                  30

Thr Cys Ala Ile Arg His Pro Cys His Asn Asn Leu Met Asn Gln Ile
             35                  40                  45

Arg Ser Gln Leu Ala Gln Leu Asn Gly Ser Ala Asn Ala Leu Phe Ile
         50                  55                  60

Leu Tyr Tyr Thr Ala Gln Gly Glu Pro Phe Pro Asn Asn Leu Asp Lys
 65                  70                  75                  80

Leu Cys Gly Pro Asn Val Thr Asp Phe Pro Pro Phe His Ala Asn Gly
                 85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Lys Leu Gly Cys Gln Leu Leu Gly Lys Tyr Lys
            180                 185                 190

Gln Ile Ile Ala Val Leu Ala Gln Ala Phe
        195                 200
```

<210> SEQ ID NO 2
<211> LENGTH: 203
<212> TYPE: PRT
<213> ORGANISM: Mus musculus

<400> SEQUENCE: 2

```
Met Lys Val Leu Ala Ala Gly Ile Val Pro Leu Leu Leu Val Leu
  1               5                  10                  15

His Trp Lys His Gly Ala Gly Ser Pro Leu Pro Ile Thr Pro Val Asn
                 20                  25                  30

Ala Thr Cys Ala Ile Arg His Pro Cys His Gly Asn Leu Met Asn Gln
             35                  40                  45

Ile Lys Asn Gln Leu Ala Gln Leu Asn Gly Ser Ala Asn Ala Leu Phe
         50                  55                  60

Ile Ser Tyr Tyr Thr Ala Gln Gly Glu Pro Phe Pro Asn Asn Val Glu
 65                  70                  75                  80

Lys Leu Cys Ala Pro Asn Met Thr Asp Phe Pro Ser Phe His Gly Asn
                 85                  90                  95

Gly Thr Glu Lys Thr Lys Leu Val Glu Leu Tyr Arg Met Val Ala Tyr
            100                 105                 110
```

```
Leu Ser Ala Ser Leu Thr Asn Ile Thr Arg Asp Gln Lys Val Leu Asn
            115                 120                 125

Pro Thr Ala Val Ser Leu Gln Val Lys Leu Asn Ala Thr Ile Asp Val
        130                 135                 140

Met Arg Gly Leu Leu Ser Asn Val Leu Cys Arg Leu Cys Asn Lys Tyr
145                 150                 155                 160

Arg Val Gly His Val Asp Val Pro Pro Val Pro Asp His Ser Asp Lys
                165                 170                 175

Glu Ala Phe Gln Arg Lys Lys Leu Gly Cys Gln Leu Leu Gly Thr Tyr
            180                 185                 190

Lys Gln Val Ile Ser Val Val Val Gln Ala Phe
        195                 200

<210> SEQ ID NO 3
<211> LENGTH: 202
<212> TYPE: PRT
<213> ORGANISM: Rattus norvegicus

<400> SEQUENCE: 3

Met Lys Val Leu Ala Ala Gly Ile Val Pro Leu Leu Leu Ile Leu His
  1               5                  10                  15

Trp Lys His Gly Ala Gly Ser Pro Leu Pro Ile Thr Pro Val Asn Ala
            20                  25                  30

Thr Cys Ala Ile Arg His Pro Cys His Gly Asn Leu Met Asn Gln Ile
        35                  40                  45

Lys Ser Gln Leu Ala Gln Leu Asn Gly Ser Ala Asn Ala Leu Phe Ile
    50                  55                  60

Ser Tyr Tyr Thr Ala Gln Gly Glu Pro Phe Pro Asn Asn Val Asp Lys
 65                  70                  75                  80

Leu Cys Ala Pro Asn Met Thr Asp Phe Pro Pro Phe His Ala Asn Gly
                85                  90                  95

Thr Glu Lys Thr Lys Leu Val Glu Leu Tyr Arg Met Val Thr Tyr Leu
            100                 105                 110

Gly Ala Ser Leu Thr Asn Ile Thr Trp Asp Gln Lys Asn Leu Asn Pro
        115                 120                 125

Thr Ala Val Ser Leu Gln Ile Lys Leu Asn Ala Thr Thr Asp Val Met
    130                 135                 140

Arg Gly Leu Leu Ser Ser Val Leu Cys Arg Leu Cys Asn Lys Tyr His
145                 150                 155                 160

Val Gly His Val Asp Val Pro Cys Val Pro Asp Asn Ser Ser Lys Glu
                165                 170                 175

Ala Phe Gln Arg Lys Lys Leu Gly Cys Gln Leu Leu Gly Thr Tyr Lys
            180                 185                 190

Gln Val Ile Ser Val Val Val Gln Ala Phe
        195                 200

<210> SEQ ID NO 4
<211> LENGTH: 202
<212> TYPE: PRT
<213> ORGANISM: Sus scrofa

<400> SEQUENCE: 4

Met Lys Val Leu Ala Ala Gly Val Val Pro Leu Leu Leu Val Leu His
  1               5                  10                  15

Trp Lys His Gly Ala Gly Ser Pro Leu Ser Ile Thr Pro Val Asn Ala
            20                  25                  30
```

```
Thr Cys Ala Thr Arg His Pro Cys His Ser Asn Leu Met Asn Gln Ile
         35                  40                  45

Lys Asn Gln Leu Ala His Val Asn Ser Ser Ala Asn Ala Leu Phe Ile
         50                  55                  60

Leu Tyr Tyr Thr Ala Gln Gly Glu Pro Phe Pro Asn Asn Leu Asp Lys
 65                  70                  75                  80

Leu Cys Gly Pro Asn Val Thr Asn Phe Pro Pro Phe His Ala Asn Gly
                 85                  90                  95

Thr Glu Lys Ala Arg Leu Val Glu Leu Tyr Arg Ile Ile Ala Tyr Leu
                100                 105                 110

Gly Ala Ser Leu Gly Asn Ile Thr Arg Asp Gln Arg Ser Leu Asn Pro
                115                 120                 125

Gly Ala Val Asn Leu His Ser Lys Leu Asn Ala Thr Ala Asp Ser Met
                130                 135                 140

Arg Gly Leu Leu Ser Asn Val Leu Cys Arg Leu Cys Asn Lys Tyr His
145                 150                 155                 160

Val Ala His Val Asp Val Ala Tyr Gly Pro Asp Thr Ser Gly Lys Asp
                165                 170                 175

Val Phe Gln Lys Lys Leu Gly Cys Gln Leu Leu Gly Lys Tyr Lys
                180                 185                 190

Gln Val Ile Ser Val Leu Ala Arg Ala Phe
                195                 200

<210> SEQ ID NO 5
<211> LENGTH: 202
<212> TYPE: PRT
<213> ORGANISM: Ovis aries

<400> SEQUENCE: 5

Met Lys Ile Leu Ala Ala Gly Val Val Pro Leu Leu Leu Val Leu His
  1               5                  10                  15

Trp Lys Pro Gly Ala Gly Ser Pro Leu Pro Ile Asn Pro Val Asn Ala
                 20                  25                  30

Thr Cys Asn Thr His His Pro Cys Pro Ser Asn Leu Met Ser Gln Ile
         35                  40                  45

Arg Ser Gln Leu Ala Gln Leu Asn Gly Thr Ala Asn Ala Leu Phe Ile
         50                  55                  60

Leu Tyr Tyr Thr Ala Gln Gly Glu Pro Phe Pro Asn Asn Leu Asp Lys
 65                  70                  75                  80

Leu Cys Gly Pro Asn Val Thr Asp Phe Pro Pro Phe Gln Pro Asn Gly
                 85                  90                  95

Thr Glu Lys Val Arg Leu Val Glu Leu Tyr Arg Ile Val Ala Tyr Leu
                100                 105                 110

Gly Thr Ala Leu Gly Asn Ile Thr Arg Asp Gln Lys Thr Leu Asn Pro
                115                 120                 125

Thr Ala His Ser Leu His Ser Lys Leu Asn Ala Thr Ala Asp Thr Leu
                130                 135                 140

Arg Gly Leu Leu Ser Asn Val Leu Cys Arg Leu Cys Ser Lys Tyr His
145                 150                 155                 160

Val Ala His Val Asp Val Ala Tyr Gly Pro Asp Thr Ser Gly Lys Asp
                165                 170                 175

Val Phe Gln Lys Lys Leu Gly Cys Gln Leu Leu Gly Lys Tyr Lys
                180                 185                 190

Gln Val Met Ala Val Leu Ala Gln Ala Phe
```

<210> SEQ ID NO 6
<211> LENGTH: 3085
<212> TYPE: DNA
<213> ORGANISM: Homo sapiens

<400> SEQUENCE: 6

| | | | | | |
|---|---|---|---|---|---|
| gagcagccaa | aaggcccgcg | gagtcgcgct | gggccgcccc | ggcgcagctg | aaccgggggc | 60 |
| cgcgcctgcc | aggccgacgg | gtctggccca | gcctggcgcc | aaggggttcg | tgcgctgtgg | 120 |
| agacgcggag | ggtcgaggcg | gcgcggcctg | agtgaaaccc | aatggaaaaa | gcatgacatt | 180 |
| tagaagtaga | agacttagct | tcaaatccct | actccttcac | ttactaattt | tgtgatttgg | 240 |
| aaatatccgc | gcaagatgtt | gacgttgcag | acttgggtag | tgcaagcctt | gtttattttc | 300 |
| ctcaccactg | aatctacagg | tgaacttcta | gatccatgtg | gttatatcag | tcctgaatct | 360 |
| ccagttgtac | aacttcattc | taatttcact | gcagtttgtg | tgctaaagga | aaaatgtatg | 420 |
| gattattttc | atgtaaatgc | taattacatt | gtctggaaaa | caaccatttt | tactattcct | 480 |
| aaggagcaat | atactatcat | aaacagaaca | gcatccagtg | tcacctttac | agatatagct | 540 |
| tcattaaata | ttcagctcac | ttgcaacatt | cttacattcg | gacagcttga | acagaatgtt | 600 |
| tatggaatca | caataatttc | aggcttgcct | ccagaaaaac | ctaaaaattt | gagttgcatt | 660 |
| gtgaacgagg | ggaagaaaat | gaggtgtgag | tgggatggtg | gaagggaaac | acacttggag | 720 |
| acaaacttca | ctttaaaatc | tgaatgggca | acacacaagt | ttgctgattg | caaagcaaaa | 780 |
| cgtgacaccc | ccacctcatg | cactgttgat | tattctactg | tgtattttgt | caacattgaa | 840 |
| gtctgggtag | aagcagagaa | tgcccttggg | aaggttacat | cagatcatat | caattttgat | 900 |
| cctgtatata | aagtgaagcc | caatccgcca | cataatttat | cagtgatcaa | ctcagaggaa | 960 |
| ctgtctagta | tcttaaaatt | gacatggacc | aacccaagta | ttaagagtgt | tataatacta | 1020 |
| aaatataaca | ttcaatatag | gaccaaagat | gcctcaactt | ggagccagat | tcctcctgaa | 1080 |
| gacacagcat | ccacccgatc | ttcattcact | gtccaagacc | ttaaaccttt | tacagaatat | 1140 |
| gtgtttagga | ttcgctgtat | gaaggaagat | ggtaagggat | actggagtga | ctggagtgaa | 1200 |
| gaagcaagtg | ggatcaccta | tgaagataga | ccatctaaag | caccaagttt | ctggtataaa | 1260 |
| atagatccat | cccatactca | aggctacaga | actgtacaac | tcgtgtggaa | gacattgcct | 1320 |
| ccttttgaag | ccaatggaaa | aatcttggat | tatgaagtga | ctctcacaag | atggaaatca | 1380 |
| catttacaaa | attacacagt | taatgccaca | aaactgacag | taaatctcac | aaatgatcgc | 1440 |
| tatctagcaa | ccctaacagt | aagaaatctt | gttggcaaat | cagatgcagc | tgttttaact | 1500 |
| atccctgcct | gtgactttca | agctactcac | cctgtaatgg | atcttaaagc | attccccaaa | 1560 |
| gataacatgc | tttgggtgga | atggactact | ccaaggggaat | ctgtaaagaa | atatatactt | 1620 |
| gagtggtgtg | tgttatcaga | taaagcaccc | tgtatcacag | actggcaaca | agaagatggt | 1680 |
| accgtgcatc | gcacctattt | aagagggaac | ttagcagaga | gcaaatgcta | tttgataaca | 1740 |
| gttactccag | tatatgctga | tggaccagga | agccctgaat | ccataaaggc | ataccttaaa | 1800 |
| caagctccac | cttccaaagg | acctactgtt | cggacaaaaa | aagtagggaa | aaacgaagct | 1860 |
| gtcttagagt | gggaccaact | tcctgttgat | gttcagaatg | gatttatcag | aaattatact | 1920 |
| atattttata | gaaccatcat | tggaaatgaa | actgctgtga | atgtggattc | ttcccacaca | 1980 |
| gaatatacat | tgtcctcttt | gactagtgac | acattgtaca | tggtacgaat | ggcagcatac | 2040 |
| acagatgaag | gtgggaagga | tggtccagaa | ttcacttttta | ctaccccaaa | gtttgctcaa | 2100 |

-continued

```
ggagaaattg aagccatagt cgtgcctgtt tgcttagcat tcctattgac aactcttctg    2160
ggagtgctgt tctgctttaa taagcgagac ctaattaaaa aacacatctg gcctaatgtt    2220
ccagatcctt caaagagtca tattgcccag tggtcacctc acactcctcc aaggcacaat    2280
tttaattcaa aagatcaaat gtattcagat ggcaatttca ctgatgtaag tgttgtggaa    2340
atagaagcaa atgacaaaaa gccttttcca gaagatctga aatcattgga cctgttcaaa    2400
aaggaaaaaa ttaatactga aggacacagc agtggtattg ggggtcttc atgcatgtca     2460 tcttctaggc caagcatttc tagcagtgat gaaaatgaat cttcacaaaa cacttcgagc    2520
actgtccagt attctaccgt ggtacacagt ggctacagac accaagttcc gtcagtccaa    2580
gtcttctcaa gatccgagtc tacccagccc ttgttagatt cagaggagcg gccagaagat    2640
ctacaattag tagatcatgt agatggcggt gatggtattt tgcccaggca acagtacttc    2700
aaacagaact gcagtcagca tgaatccagt ccagatattt cacattttga aaggtcaaag    2760
caagtttcat cagtcaatga ggaagatttt gttagactta aacagcagat ttcagatcat    2820
atttcacaat cctgtggatc tgggcaaatg aaaatgtttc aggaagtttc tgcagcagat    2880
gcttttggtc caggtactga gggacaagta gaaagatttg aaacagttgg catggaggct    2940
gcgactgatg aaggcatgcc taaaagttac ttaccacaga ctgtacggca aggcggctac    3000
atgcctcagt gaaggactag tagttcctgc tacaacttca gcagtaccta taagtaaag     3060 ctaaaatgat tttatctgtg aattc                                         3085
```

<210> SEQ ID NO 7
<211> LENGTH: 918
<212> TYPE: PRT
<213> ORGANISM: Homo sapiens

<400> SEQUENCE: 7

```
Met Leu Thr Leu Gln Thr Trp Val Val Gln Ala Leu Phe Ile Phe Leu
  1               5                  10                  15

Thr Thr Glu Ser Thr Gly Glu Leu Leu Asp Pro Cys Gly Tyr Ile Ser
             20                  25                  30

Pro Glu Ser Pro Val Val Gln Leu His Ser Asn Phe Thr Ala Val Cys
         35                  40                  45

Val Leu Lys Glu Lys Cys Met Asp Tyr Phe His Val Asn Ala Asn Tyr
     50                  55                  60

Ile Val Trp Lys Thr Asn His Phe Thr Ile Pro Lys Glu Gln Tyr Thr
 65                  70                  75                  80

Ile Ile Asn Arg Thr Ala Ser Ser Val Thr Phe Thr Asp Ile Ala Ser
                 85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190
```

```
Asn Ile Glu Val Trp Val Glu Ala Glu Asn Ala Leu Gly Lys Val Thr
        195                 200                 205
Ser Asp His Ile Asn Phe Asp Pro Val Tyr Lys Val Lys Pro Asn Pro
    210                 215                 220
Pro His Asn Leu Ser Val Ile Asn Ser Glu Leu Ser Ser Ile Leu
225                 230                 235                 240
Lys Leu Thr Trp Thr Asn Pro Ser Ile Lys Ser Val Ile Ile Leu Lys
                245                 250                 255
Tyr Asn Ile Gln Tyr Arg Thr Lys Asp Ala Ser Thr Trp Ser Gln Ile
            260                 265                 270
Pro Pro Glu Asp Thr Ala Ser Thr Arg Ser Ser Phe Thr Val Gln Asp
        275                 280                 285
Leu Lys Pro Phe Thr Glu Tyr Val Phe Arg Ile Arg Cys Met Lys Glu
    290                 295                 300
Asp Gly Lys Gly Tyr Trp Ser Asp Trp Ser Glu Glu Ala Ser Gly Ile
305                 310                 315                 320
Thr Tyr Glu Asp Arg Pro Ser Lys Ala Pro Ser Phe Trp Tyr Lys Ile
                325                 330                 335
Asp Pro Ser His Thr Gln Gly Tyr Arg Thr Val Gln Leu Val Trp Lys
            340                 345                 350
Thr Leu Pro Pro Phe Glu Ala Asn Gly Lys Ile Leu Asp Tyr Glu Val
        355                 360                 365
Thr Leu Thr Arg Trp Lys Ser His Leu Gln Asn Tyr Thr Val Asn Ala
    370                 375                 380
Thr Lys Leu Thr Val Asn Leu Thr Asn Asp Arg Tyr Leu Ala Thr Leu
385                 390                 395                 400
Thr Val Arg Asn Leu Val Gly Lys Ser Asp Ala Ala Val Leu Thr Ile
                405                 410                 415
Pro Ala Cys Asp Phe Gln Ala Thr His Pro Val Met Asp Leu Lys Ala
            420                 425                 430
Phe Pro Lys Asp Asn Met Leu Trp Val Glu Trp Thr Thr Pro Arg Glu
        435                 440                 445
Ser Val Lys Lys Tyr Ile Leu Glu Trp Cys Val Leu Ser Asp Lys Ala
    450                 455                 460
Pro Cys Ile Thr Asp Trp Gln Gln Glu Asp Gly Thr Val His Arg Thr
465                 470                 475                 480
Tyr Leu Arg Gly Asn Leu Ala Glu Ser Lys Cys Tyr Leu Ile Thr Val
                485                 490                 495
Thr Pro Val Tyr Ala Asp Gly Pro Gly Ser Pro Glu Ser Ile Lys Ala
            500                 505                 510
Tyr Leu Lys Gln Ala Pro Pro Ser Lys Gly Pro Thr Val Arg Thr Lys
        515                 520                 525
Lys Val Gly Lys Asn Glu Ala Val Leu Glu Trp Asp Gln Leu Pro Val
    530                 535                 540
Asp Val Gln Asn Gly Phe Ile Arg Asn Tyr Thr Ile Phe Tyr Arg Thr
545                 550                 555                 560
Ile Ile Gly Asn Glu Thr Ala Val Asn Val Asp Ser Ser His Thr Glu
                565                 570                 575
Tyr Thr Leu Ser Ser Leu Thr Ser Asp Thr Leu Tyr Met Val Arg Met
            580                 585                 590
Ala Ala Tyr Thr Asp Glu Gly Gly Lys Asp Gly Pro Glu Phe Thr Phe
        595                 600                 605
Thr Thr Pro Lys Phe Ala Gln Gly Glu Ile Glu Ala Ile Val Val Pro
```

-continued

```
                    610                 615                 620
Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                    645                 650                 655

Asp Pro Ser Lys Ser His Ile Ala Gln Trp Ser Pro His Thr Pro Pro
                660                 665                 670

Arg His Asn Phe Asn Ser Lys Asp Gln Met Tyr Ser Asp Gly Asn Phe
                675                 680                 685

Thr Asp Val Ser Val Val Glu Ile Glu Ala Asn Asp Lys Lys Pro Phe
            690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                    725                 730                 735

Ser Arg Pro Ser Ile Ser Ser Asp Glu Asn Glu Ser Ser Gln Asn
                740                 745                 750

Thr Ser Ser Thr Val Gln Tyr Ser Thr Val Val His Ser Gly Tyr Arg
            755                 760                 765

His Gln Val Pro Ser Val Gln Val Phe Ser Arg Ser Glu Ser Thr Gln
            770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                    805                 810                 815

Gln Asn Cys Ser Gln His Glu Ser Ser Pro Asp Ile Ser His Phe Glu
                820                 825                 830

Arg Ser Lys Gln Val Ser Ser Val Asn Glu Glu Asp Phe Val Arg Leu
            835                 840                 845

Lys Gln Gln Ile Ser Asp His Ile Ser Gln Ser Cys Gly Ser Gly Gln
            850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                    885                 890                 895

Thr Asp Glu Gly Met Pro Lys Ser Tyr Leu Pro Gln Thr Val Arg Gln
                900                 905                 910

Gly Gly Tyr Met Pro Gln
            915
```

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 8

```
Glu Lys Arg Glu Ala Glu Ala Tyr
  1               5
```

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic -continued

```
<400> SEQUENCE: 9

Arg Gly Gly Gly Gly Ser Gly Gly Gly Ser Val Glu
 1               5                  10
```

METHODS FOR IN VITRO FERTILIZATION

FIELD OF THE INVENTION

The present invention relates to compositions and methods for in vitro fertilization (IVF), and in particular, enhancing implantation frequencies and blocking implantation in mammals (including but not limited to humans) using LIF and LIF antagonists.

BACKGROUND

Infertility is a problem that afflicts approximately 9% of couples in the United States who wish to have children. The causes of infertility are many and varied. Whatever the cause in the particular case, treatment can be very expensive. Indeed, it is estimated that the annual cost of treating infertile couples in the United States is approximately 1 billion dollars.

Frequently, treatment involves the use of in vitro fertilization (IVF) in which eggs from the woman are recovered and fertilized with the male's sperm. The resulting embryo(s) are then surgically transferred back to the woman's uterus for development to continue. However, only about 25% (at best) of the transplanted embryos implant properly with even fewer resulting in live birth. Failure of transplanted embryos to implant is thus a major difficulty in treating the larger problem of infertility.

One obvious approach to improving the chance of success is to increase the number of embryos being implanted. While the use of multiple embryos (e.g., the transfer of up to four embryos to the uterus at the same time) increases the chances of one of them implanting, the recipient also runs the risk of multiple implants and consequently multiple births. See Elsner et al., *Am J Obstet Gynecol* 177:350-355 (1997). This method is also unsatisfactory in that if the uterus is physically and chemically unprepared to receive embryos because the hormonal regulation is dysfunctional, simply transplanting more embryos will not solve the problem.

A number of hormones (e.g. estrogen, progesterone, etc.) have been identified as having a role in the preparation of the uterus to receive a transplanted embryo, and thus many attempts to improve implantation frequency have focused on the regulation of these hormones. For example, estrogen appears to play a significant role in regulating uterine receptivity to embryo implantation, and thus one treatment of implantation failure is to regulate (e.g. increase) the estrogen level of the host. This approach to treatment frequently backfires, however, as it is thought that this can cause implantation failure due to improper uterine physiology and chemical receptivity induced by the estrogen treatment. Moreover, increased levels of estrogens employed during IVF treatment have been implicated in severe complications of the Ovarian Hyperstimulation Syndrome (OHS). See e.g. MacDougall et al., *Hum Reprod* 7:597-600 (1992).

What is needed is an effective substitute for the standard hormonal treatment currently used to increase uterine receptivity to embryo implantation. A one-time, non-invasive direct administration of an estrogen substitute would allow increased use and effectiveness of treatment of implantation failure, without the side effects of increased estrogen levels.

DEFINITIONS

The term "hematopoietic cytokine receptor family" is the recognized family of receptors [see e.g. T. Taga and T. Kishimoto, "Cytokine receptors and signal transduction," *FASAB J.* 6:3387 (1992)] having structural similarity to IL-6-R, and more particularly, having structural similarity with respect to the approximately 200 amino acid-homologous regions of IL-6-R, said region characterized by four conserved cysteine residues in the amino-terminal half and a WSXWS motif at is carboxyl-terminal end (wherein W is Trp; S is Ser; and X is a nonconserved amino acid). Members of this family include IL-2-R, IL-3-R, IL-4-R, IL-5-R, IL-6-R, IL-7R, IL-9-R, EPO-R, G-CSF-R, GM-CSF-R and LIF-R.

A subset of the above-named receptors typically exist as a "receptor complex" comprising the above-named molecule in association with another protein called gp130. Thus, the corresponding ligands that bind the above-named receptors typically bind the complex. Thus, the present invention contemplates "a cytokine capable of binding to a receptor complex comprising a member of the hematopoietic cytokine receptor family." Examples of such ligands are IL-6 and LIF. Other examples include Oncostatin M. Ciliary Neurotrophic Factor and Cardiotrophin-1.

The present invention also contemplates molecules that are simply capable of binding to gp130, such molecules useful for the treatment of females to enhance implantation frequencies.

An "estrogen-free" composition contains no detectable estrogen (e.g. detectable by immunological assay). A "substantially estrogen-free" composition contains only background amounts of estrogen. A female "subsequently" not treated with estrogen is a female who, subsequent to the claimed method step (e.g. the step of introducing an embryo into said female), does not receive estrogen. A female "that has not been treated with estrogen" is a female who has received no exogenous estrogen prior to the first step of the claimed method.

SUMMARY OF THE INVENTION

The present invention relates to compositions and methods for in vitro fertilization (VF), and in particular, enhancing implantation frequencies and blocking implantation in mammals (including but not limited to humans) using LIF and LIF antagonists, respectively.

With respect to enhancing implantation frequencies, the present invention contemplates treatment of females with the cytokine Leukemia Inhibitory Factor (LIF). The present invention contemplates the direct injection of LIF, which leads to the embryo's normal development to birth and also, the use of LIF as a replacement to using estrogen for in vitro fertilization.

Figure 1:
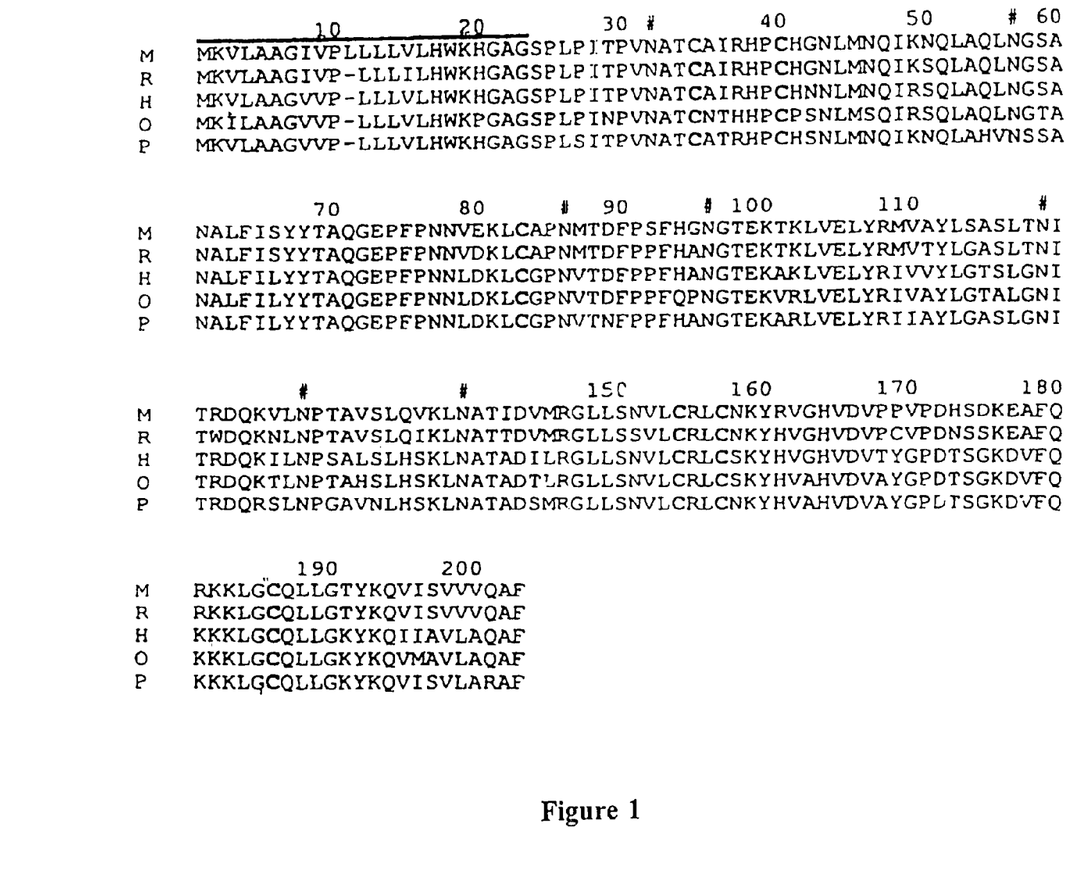
FIG. 1 shows an alignment of the predicted amino acid sequence of human (SEQ ID NO:1), murine (SEQ ID NO:2), rat (SEQ ID NO:3), porcine (SEQ ID NO:4) and ovine (SEQ ID NO:5) versions of LIF (the predicted signal sequence is shown by a solid line above the sequence and potential N-linked glycosylation sites are indicated by #).

It is not intended that the present invention be limited to only one type of LIF. A variety of LIF proteins are contemplated, including but not limited to LIF from human (SEQ ID NO:1), murine (SEQ ID NO:2), rat (SEQ ID NO:3), porcine (SEQ ID NO:4) and ovine (SEQ ID NO:5) (see FIG. 1). In a preferred embodiment, the LIF administered according to the present invention is recombinantly produced LIF.

It is also not intended that the present invention be limited to LIF. In one embodiment, the present invention contemplates a method, comprising: a) providing i) a female to be implanted with at least one embryo, and ii) an estrogen-free composition, comprising a cytokine capable of binding to a receptor complex comprising a member of the hematopoietic cytokine receptor family; and b) administering said estrogen-free composition to said female under conditions such that said embryo implants. In a preferred embodiment, said cytokine is LIF and said embryo is an in vitro fertilized embryo.

In a preferred embodiment, the present invention contemplates a method, comprising: a) providing i) an embryo, ii) a female to be implanted with said embryo, and iii) an estrogen-free composition, comprising a cytokine capable of binding to a receptor complex comprising a member of the hematopoietic cytokine receptor family; b) introducing said embryo into said female, said female subsequently not treated with exogenous estrogen (i.e. estrogen given exogenously) and c) administering said estrogen-free composition to said female under conditions such that said embryo implants. In a preferred embodiment, said cytokine is LIF and said embryo is an in vitro fertilized embryo.

It is also not intended that the present invention be limited to LIF. In one embodiment, the present invention contemplates a method, comprising: a) providing i) a female that has not been treated with exogenous estrogen, said female to be implanted with at least one embryo, and ii) an estrogen-free composition, comprising a cytokine capable of binding to a receptor complex comprising a member of the hematopoietic cytokine receptor family; and b) administering said estrogen-free composition to said female under conditions such that said embryo implants. In a preferred embodiment, said cytokine is LIF and said embryo is an in vitro fertilized embryo.

In another embodiment, the present invention contemplates a method, comprising: a) providing i) a female that has not been treated with exogenous estrogen, said female to be implanted with at least one embryo, and ii) an estrogen-free composition, comprising a ligand capable of binding to gp130; and b) administering said estrogen-free composition to said female under conditions such that said embryo implants. In a preferred embodiment, said embryo is an in vitro fertilized embryo.

DESCRIPTION OF THE INVENTION

The present invention relates to compositions and methods for in vitro fertilization (IVF), and in particular, enhancing implantation frequencies and blocking implantation in mammals (including but not limited to humans) using LIF and LIF antagonists, respectively.

With respect to enhancing implantation frequencies, the present invention contemplates treatment of females with the cytokine Leukemia Inhibitory Factor (LIF).

LIF has been identified as having a role in the implantation process and attempts have been made to increase implantation frequency by either culturing the embryos in LIF-containing medium (see e.g. U.S. Pat. No. 5,366,888 to Fry et al., hereby incorporated by reference) or continuously administering LIF to the host. See Stewart et al., *Nature* 359:76-79 (1992). These techniques have met with some success, but are inferior in that surgery is involved in the implantation of a micro-pump and that they do not address the problem caused by the estrogen treatment.

A. Leukemia Inhibitor Factor (LIF) and the LIF Receptor

LIF is a member of a family of proteins (the IL-6 family of cytokines) that show some structural similarities. They sometimes have similar effects on the same cell, because they can bind to each other's receptors and stimulate them. What all these factors have in common is that for their specific receptors to function properly, it appears that they have to associate with the gp130 protein. Without being limited to any particular mechanism, the present invention contemplates that other members of the IL-6 family of cytokines will have the same effects on embryo implantation as LIF, and in particular, those members that require the LIF receptors are expected to be particularly effective.

Figure 2:
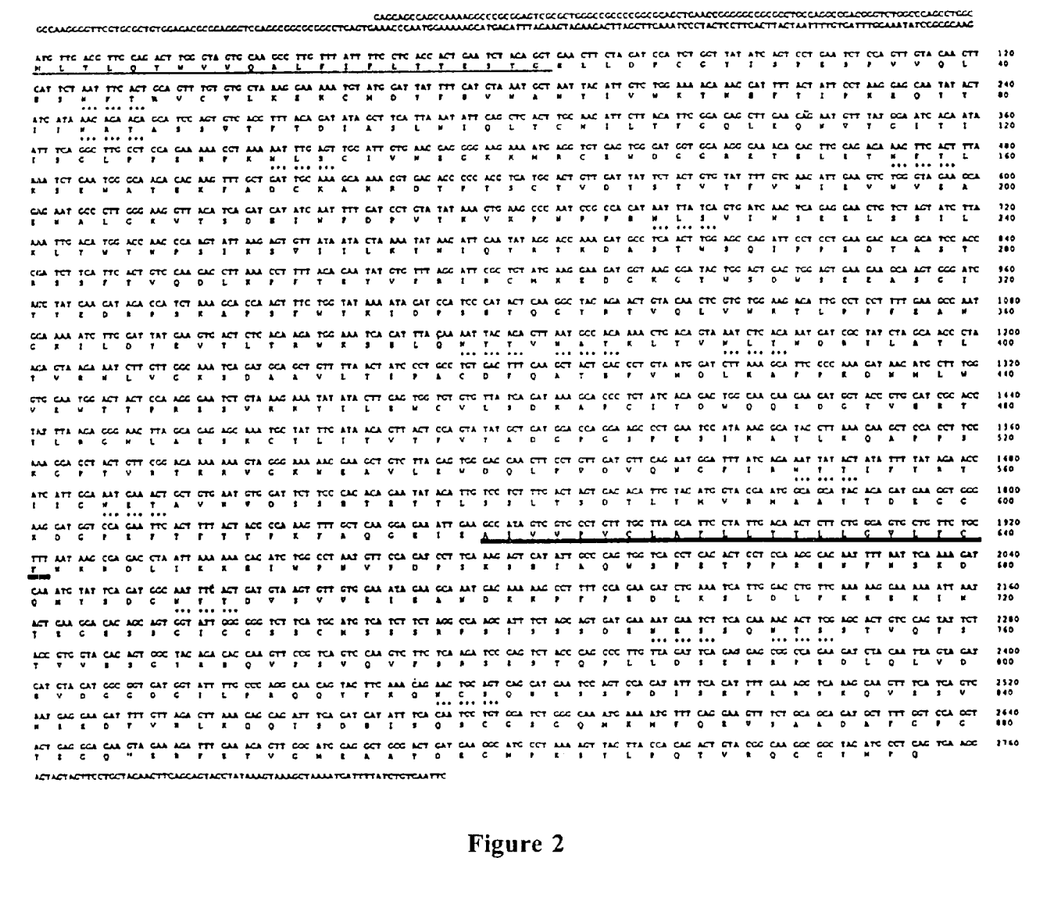
FIG. 2 shows the nucleic acid sequence (SEQ ID NO:6) and amino acid sequence (SEQ ID NO:7) of gp130.
Figure 3:
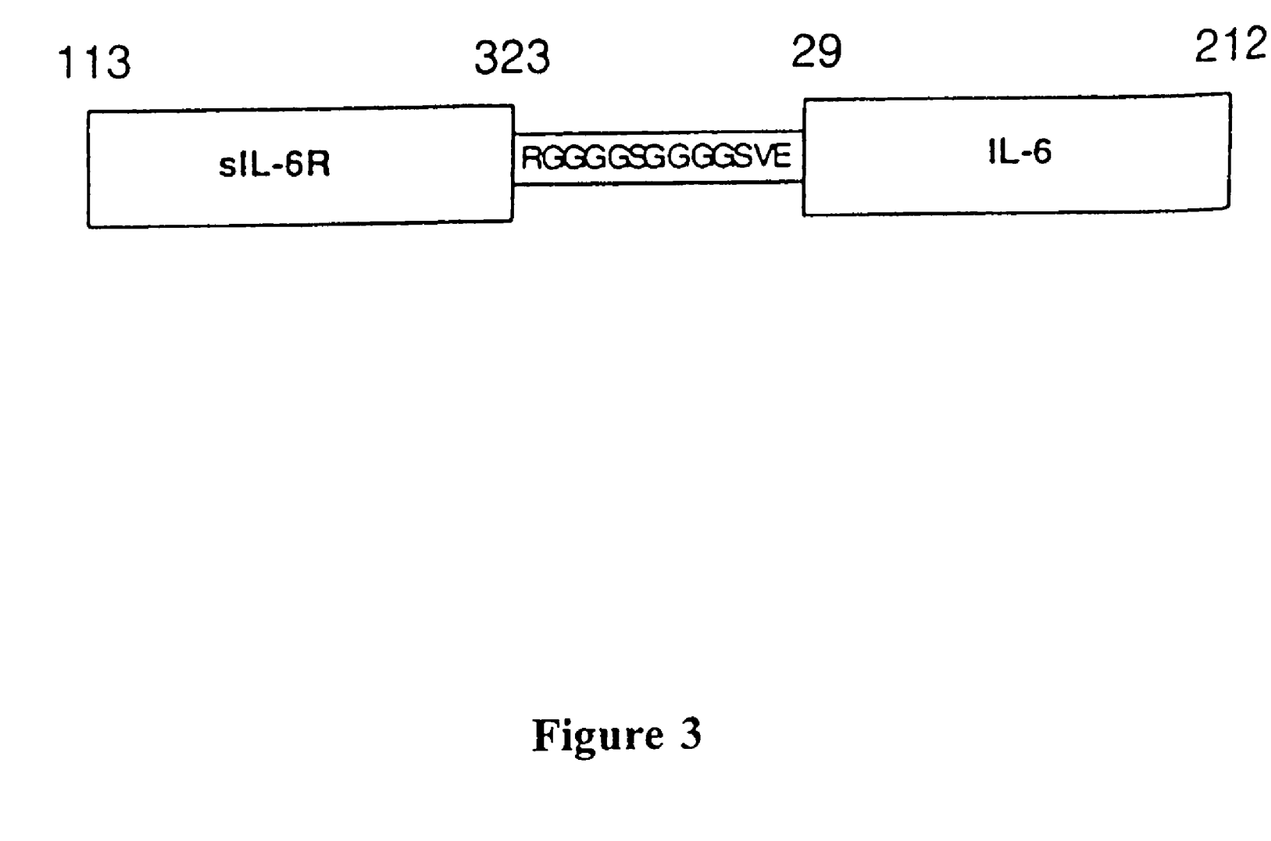
FIG. 3 schematically shows the cDNA encoding a fusion protein of IL-6 and sIL-6R.

The receptor complex that LIF binds to at the cell surface is comprised of two proteins: the LIF receptorα and another protein called gp130 (see FIG. 2). When LIF binds to the LIF receptorα this complex then binds to gp130 which causes the receptor to "fire" so activating a number of processes and responses in the cells to which LIF has bound. While the present invention is not limited to any particular mechanism, this association of LIF+LIF receptorα with gp130 appears to be essential for the whole receptor complex to function properly.

As noted above, the present invention contemplates the administration of ligands capable of binding gp130. Such compounds can be readily screened for and tested in a binding assay with gp130.

B. LIF Antagonists

In one embodiment, the present invention relates to compositions and methods for blocking implantation in mammals (including but not limited to humans) using LIF antagonists. A variety of LIF antagonists are contemplated, including but not limited to mutant versions of LIF and antibodies to LIF. Mutant LIF can be LIF with amino acid modifications, substitutions and deletions.

In one embodiment, LIF is altered such that it cannot bind to the LIF receptor complex. Such altered LIF molecules are readily tested (usually by labeling them) for binding to the LIF receptor on cells. Such an altered LIF molecule can then be used to block implantation in normal female mammals (e.g. females having normal levels of functional LIF).

C. Formulations and Preparations

It is not intended that the present invention be limited by the particular nature of the therapeutic preparation used for administration of the cytokines useful for enhanced implantation. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Oral formulations for cancer usually will include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%.

The compositions are also prepared as injectables, either as liquid solutions or suspensions: solid forms suitable for solution in, or suspension in, liquid prior to injection may also be prepared.

The antagonists of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

EXPERIMENTAL

The following examples serve to illustrate certain preferred embodiments and aspects of the present invention and are not to be construed as limiting the scope thereof.

Example 1

In this example, LIF is shown to be useful as a replacement for estrogen. Mice were ovariectomized and allowed to recover for 18 days before starting experimental manipulation. Priming of the uterus by steroid hormones was started by the injection of 100 ng of Estrogen on each of 3 consecutive days. On the 6th day the mice were given a single injection of Progesterone in the form of Depo-Provera. Three days later an average of 6 blastocysts, either directly isolated from females or from cultures started the previous day when the embryos were at the 8-cell stage were surgically transferred to the right uterine horn. After the mice had recovered from surgery they were either given 1 injection of 40 ng of estrogen or 3 injections, 1 hour apart, of 5 µg LIF. Four days later (equivalent to Day 7-8 of pregnancy) the mice were sacrificed for analysis, and the implantation sites recovered. Examination of the deciduas revealed that they contained morphologically normal embryos at the right stage of development.

The results presentedd in Table 1 using this particular experimental protocol reveal that the injection of LIF can unequivocally replace the injection of estrogen for inducing embryo implantation. In turn this demonstrates that LIF could be used as an alternative to already established hormonal treatments for increasing the frequency of obtaining successful implantations and viable embryonic development in the treatment of human infertility following In Vitro Fertilization and transfer of the resulting embryo to the mother's uterus.

TABLE 1

Injection of Recombinant LIF Substitutes for Nidatory (implantational) Estrogen at inducing Blastocyst Implantation

| Blastocyst Type at time of Transfer | Implantation Agent | Nos. Blastocysts Transferred (Nos. of recipients) | Nos. Pregnant | Nos. Implanted |
|---|---|---|---|---|
| D4 direct | E2 | 36 (6) | 3 | 11 |
| D4 cultured | E2 | 36 (6) | 4 | 16 |
| D4 direct | LIF | 36 (6) | 6 | 30 |
| D4 cultured | LIF | 42 (7) | 5 | 16 |
| D4 direct | Saline (control) | 30 | 0 | 0 |

Example 2

In this example, a soluble IL-6 ligand/receptor fusion protein (sIL-6RFP) is tested. The sequences for IL-6 and IL-6R are known. See e.g. K. Yamasaki et al. "Cloning and expression of the human Interleukin-6 (BSF-2/IFN β2) receptor" Science 241: 825-828 (1988). A cassette (FIG. 2) consisting of human sIL-6R cDNA (corresponding to amino acid residues 113-323) and human IL-6 cDNA (corresponding to amino acid residues 29-212) fused by a synthetic DNA linker coding for the amino acid sequence Arg-Gly-Gly-Gly-Gly-Ser-Gly-Gly-Gly-Gly-Ser-Val-Glu (SEQ ID NO:9) was constructed by the PCR technique and cloned into the Pichia pastoris expression vector pPIC9 (Invitrogen, San Diego, Calif.) using the restriction enzymes SnaBI and EcoRI. Cleavage of the signal peptide in transfected yeast cells leads to the secretion of the fusion protein with an $NH_2$-terminal extension of 8 amino acid residues (Glu-Lys-Arg-Glu-Ala-Glu-Ala-Tyr; SEQ ID NO:8). The fusion protein was purified from yeast supernatants by anion-exchange chromatography and gel filtration and visualized by SDS-PAGE and silver staining.

This fusion protein is essentially a hybrid protein comprised of IL-6 already bound to its specific receptor. This complex will then bind to any cell that has gp130 and activate the cell. To test the protein, pseudopregnant wild type mice were ovariectomized on Day 3 of pregnancy. Six females had ten 8-cell stage embryos surgically transferred to their right uterine horn and were injected with progesterone. Five days later 3 mice were each injected with 2 µg of sIL-6RFP and the other 3 were injected with a saline control. Three days later the mice were examined for the presence of implanted embryos. The results are shown in Table 2.

TABLE 2

| Treatment | Nos. of Mice Carrying 10 Embryos Each | Nos. with Implantation Sites | Nos. of Embryos Implanted |
|---|---|---|---|
| sIL-6RFP | 3 | 2 | 8 and 10 |
| Saline | 3 | 0 | Total of 15 unimplanted embryos recovered |

The results show that this fusion protein is effective at inducing embryo implantation in the absence of estrogen, and thus can be used as an alternative to LIF.

We claim:

1. A method, comprising:
   a) providing
      i) a female mammal that has not been treated with exogenous estrogen, said female to be implanted with at least one embryo and
      ii) an estrogen-free composition, comprising Leukemia Inhibitory Factor; and
   b) administering said estrogen-free composition to said female after transfer of the at least one embryo into the female's uterus, such that said embryo implants.

2. The method of claim 1, wherein said female mammal is a human.

3. The method of claim 1, wherein said embryo is an in vitro fertilized embryo.

* * * * *